US010646528B2

(12) United States Patent
Jin et al.

(10) Patent No.: US 10,646,528 B2
(45) Date of Patent: May 12, 2020

(54) METHOD FOR PREPARING EXTRACT OF GENUS *PANAX* INCLUDING WILD GINSENG OR GINSENG, OR CAMBIAL MERISTEMATIC CELLS DERIVED FROM GENUS *PANAX* OR EXTRACT THEREOF CONTAINING RARE GINSENOSIDES IN HIGH QUANTITY

(71) Applicant: WELLKEY HOLDINGS LIMITED, Road Town Tortola (VG)

(72) Inventors: Young-Woo Jin, Jeollabuk-do (KR); Eun-Kyong Lee, Jeollabuk-do (KR); Young Mi Lee, Jeollabuk-do (KR); Il Seok Oh, Jeollabuk-do (KR)

(73) Assignee: WELLKEY HOLDINGS LIMITED, Tortola (VG)

( * ) Notice: Subject to any disclaimer, the term of this patent is extended or adjusted under 35 U.S.C. 154(b) by 414 days.

(21) Appl. No.: 15/502,423

(22) PCT Filed: Aug. 24, 2015

(86) PCT No.: PCT/KR2015/008800
§ 371 (c)(1),
(2) Date: Feb. 7, 2017

(87) PCT Pub. No.: WO2016/028129
PCT Pub. Date: Feb. 25, 2016

(65) Prior Publication Data
US 2017/0232049 A1 Aug. 17, 2017

(30) Foreign Application Priority Data
Aug. 22, 2014 (KR) .................. 10-2014-0109735

(51) Int. Cl.
A61K 36/258 (2006.01)
C12N 5/04 (2006.01)
C12P 19/56 (2006.01)
C12P 33/00 (2006.01)
A61K 31/575 (2006.01)
A61K 31/704 (2006.01)

(52) U.S. Cl.
CPC .......... *A61K 36/258* (2013.01); *A61K 31/575* (2013.01); *A61K 31/704* (2013.01); *C12N 5/04* (2013.01); *C12P 19/56* (2013.01); *C12P 33/00* (2013.01)

(58) Field of Classification Search
CPC .. A61K 31/575; A61K 31/704; A61K 36/258; C12N 5/04; C12P 19/56; C12P 33/00
See application file for complete search history.

(56) References Cited

U.S. PATENT DOCUMENTS

2003/0190378 A1  10/2003  Kim et al.

FOREIGN PATENT DOCUMENTS

| EP | 2399596 A2 | 12/2011 |
|---|---|---|
| JP | S62158490 A | 7/1987 |
| JP | 11501322 A | 2/1999 |
| JP | 2007520418 A | 7/2007 |
| JP | 2011522884 A | 8/2011 |
| JP | 2011530583 A | 12/2011 |
| JP | 2012504121 A1 | 2/2012 |
| JP | 2012507579 A | 3/2012 |
| KR | 10-0192678 B1 | 6/1999 |
| KR | 1020030080999 A | 10/2003 |
| KR | 10-2004-0110960 A | 12/2004 |
| KR | 10-2010-0021369 A | 2/2010 |
| KR | 10-1064518 B1 | 9/2011 |
| KR | 1020110123311 A | 11/2011 |
| KR | 20130060837 A | 6/2013 |
| KR | 10-2014-0066480 A | 6/2014 |
| RU | 2514008 C1 | 4/2014 |
| WO | WO2006098604 A1 | 9/2006 |
| WO | WO2013176512 A1 | 11/2013 |

OTHER PUBLICATIONS

Stepanenko, B., et al., "Always in the Tone Ginsegold", "Fito Eastern Wisdom", 2012, pp. 8-10, No. 33.
Stepanenko, B.B., et al, "Always in the Tone Ginsegold", "Fito Eastern Wisdom", 2012, Page(s) English Translation, No. 33.
Ahn, H., et al., "Panax Ginseng Extract Rich in Ginsenoside Protopanaxatriol Offers Combinatorial Effects in Nitric Oxide Production Via Multiple Signaling Pathways", 2013, pp. 1-7, vol. 2, No. 96.
Attele, A., et al., "Ginseng Pharmacology: Multiple Constituents and Multiple Actions", "Biochemical Pharmacology", 1999, pp. 1685-1693, vol. 58.
Lee, E., et al, "Cultured Cambial Meristematic Cells as a Source of Plant Natural Products", "Nature Biotechnology", Nov. 2010, pp. 1213-1217, vol. 28, No. 11.

(Continued)

*Primary Examiner* — Aaron J Kosar
(74) *Attorney, Agent, or Firm* — Hultquist, PLLC; Steven J. Hultquist

(57) ABSTRACT

The present invention relates to a method for increasing the content of rare ginsenosides in preparing an extract of genus *Panax* including wild ginseng or ginseng, cambial meristematic cells of genus *Panax* or an extract thereof, a ginseng extract prepared by the method, cambial meristematic cells (CMCs) of genus *Panax* or an extract thereof prepared by the method, and to a composition comprising the same. Specifically, the present invention relates to a method for increasing the content of rare ginsenosides such as Rh2, in preparing an extract of genus *Panax* including wild ginseng or ginseng, cambial meristematic cells of genus *Panax* or an extract thereof, a ginseng extract prepared by the method, cambial meristematic cells (CMCs) of genus *Panax* or an extract thereof prepared by the method, and to a composition for improving blood circulation or a composition for improving liver function, which contains, as an active ingredient, a extract of genus *Panax*, cambial meristematic cells of genus *Panax* or an extract thereof, prepared by the method.

15 Claims, 13 Drawing Sheets

(56) References Cited

OTHER PUBLICATIONS

Rodin, I., et al., "Modem Methods of Identifying and Determining Ginsenosides", "Moscow University Chemistry Bulletin", 2013, pp. 127-142, vol. 68, No. 3.
Toh, D., et al., "Anti-Proliferative Effects of Raw and Steamed Extracts of Panax Notoginseng and its Ginsenoside Constituents on Human Liver Cancer Cells", "Chinese Medicine", 2011, pp. 1-9, vol. 6, No. 4.
Wang, C., et al, "Steamed American Ginseng Berry: Ginsenoside Analyses and Anticancer Activities", "J. Agric. Food Chem.", 2006, pp. 9936-9942, vol. 54.
Kim, W.Y., et al., "Steaming of Ginseng at High Temperature Enhances Biological Activity", "Journal of Natural Products", Oct. 21, 2000, pp. 1702-1704, vol. 63, No. 12, Publisher: American Chemical Society and American Society of Pharmacognosy.

1 : Control
2 : Vehicle + GalN
3 : Wild ginseng CMCs 75 mg/kg + GalN
4 : Wild ginseng CMCs 150 mg/kg + GalN
5 : Wild ginseng CMCs 300 mg/kg + GalN
6 : Silymarin 50 mg/kg + GalN

FIG. 10

Converted rare ginsenosides in ginseng extracts

|  | Batch 1 | | Batch 2 | |
| --- | --- | --- | --- | --- |
|  | Before heat treatment | After heat treatment | Before heat treatment | After heat treatment |
| Rg1+Re | 95.39 | 0.00 | 0.00 | 0.00 |
| Rb1 | 33.34 | 0.00 | 36.99 | 0.00 |
| Rc | 94.02 | 0.00 | 145.71 | 0.00 |
| Rb2 | 26.70 | 0.00 | 28.74 | 0.00 |
| Rd | 40.37 | 0.00 | 14.56 | 0.00 |
| Gypenoside XVII | 6.41 | 0.00 | 12.90 | 0.00 |
| F2 | 10.75 | 0.00 | 11.45 | 0.00 |
| Sum | 306.98 | 0.00 | 250.34 | 0.00 |
| Rg3 | 9.21 | 96.02 | 6.59 | 117.92 |
| Rg5 | 4.94 | 58.81 | 2.90 | 80.02 |
| Compound K | 0.00 | 0.00 | 0.00 | 0.00 |
| Rh2 | 1.77 | 30.83 | 2.15 | 60.37 |
| PPD | 0.00 | 1.84 | 0.00 | 4.27 |
| Sum | 15.92 | 187.50 | 11.65 | 262.58 |

\* Each numerical value indicates the content (mg) of ginsenoside in 1 g of ginseng extract powder.

FIG. 11

| 85°C/ 24h | Control | 1:30 | 1:50 | 1:100 | 1:150 | 1:200 |
|---|---|---|---|---|---|---|
| Rb1 | 15.61 | 4.42 | 0.28 | 0.25 | 0.00 | 0.00 |
| Rc | 4.95 | 1.40 | 0.72 | 0.15 | 0.00 | 0.00 |
| Rb2 | 2.52 | 1.28 | 0.58 | 0.12 | 0.00 | 0.00 |
| Rd | 1.85 | 4.57 | 3.11 | 1.05 | 0.51 | 0.29 |
| Gypenoside XVII | 0.14 | 6.13 | 3.95 | 1.00 | 0.43 | 0.25 |
| F2 | 0 | 0.86 | 0.89 | 0.85 | 0.81 | 0.72 |
| Rg3 | 0 | 26.19 | 30.83 | 33.95 | 34.10 | 31.19 |
| Rk1 | 0 | 7.14 | 7.55 | 7.63 | 7.41 | 7.00 |
| Rg5 | 0 | 13.91 | 15.50 | 15.79 | 15.32 | 14.44 |
| Rh2 | 0 | 15.92 | 19.18 | 22.98 | 23.91 | 22.57 |
| Sum | 25.1 | 81.8 | 82.6 | 83.8 | 82.5 | 76.5 |

* Each numerical value indicates the content (mg) of ginsenoside in 1 g of dried wild ginseng CMCs.

FIG. 12

| 1 : 100 / 24hr | Control | 85°C | 95°C | 115°C |
|---|---|---|---|---|
| Rb1 | 15.61 | 0.25 | 0.00 | 0.00 |
| Rc | 4.95 | 0.15 | 0.00 | 0.00 |
| Rb2 | 2.52 | 0.12 | 0.00 | 0.00 |
| Rd | 1.85 | 1.05 | 0.00 | 0.00 |
| Gypenoside XVII | 0.14 | 1.00 | 0.00 | 0.00 |
| F2 | 0 | 0.85 | 1.21 | 3.10 |
| Rg3 | 0 | 33.95 | 41.95 | 38.75 |
| Rk1 | 0 | 7.63 | 11.29 | 20.30 |
| Rg5 | 0 | 15.79 | 22.97 | 40.87 |
| Rh2 | 0 | 22.98 | 31.41 | 36.11 |
| Sum | 25.1 | 83.8 | 108.8 | 139.1 |

\* Each numerical value indicates the content (mg) of ginsenoside in 1 g of dried wild ginseng CMCs.

FIG. 13

| 1 : 100 / 85°C | Control | 24h | 48h | 72h |
|---|---|---|---|---|
| Rb1 | 15.61 | 0.25 | 0.00 | 0.00 |
| Rc | 4.95 | 0.15 | 0.00 | 0.00 |
| Rb2 | 2.52 | 0.12 | 0.00 | 0.00 |
| Rd | 1.85 | 1.05 | 0.00 | 0.00 |
| Gypenoside XVII | 0.14 | 1.00 | 0.00 | 0.00 |
| F2 | 0 | 0.85 | 0.00 | 0.00 |
| Rg3 | 0 | 33.95 | 37.79 | 38.65 |
| Rk1 | 0 | 7.63 | 8.83 | 9.15 |
| Rg5 | 0 | 15.79 | 17.79 | 18.11 |
| Rh2 | 0 | 22.98 | 28.63 | 32.00 |
| Sum | 25.1 | 83.8 | 93.0 | 97.9 |

* Each numerical value indicates the content (mg) of ginsenoside in 1 g of dried wild ginseng CMCs.

FIG. 14

| Rare ginsenosides | Contents, mg/g (dry cell weight) | | |
|---|---|---|---|
| | A. 5 days of static culture | B. 9 days of s static culture | C. 13 days of static culture |
| Rg3 | 54.05 | 46.65 | 43.94 |
| Rh2 | 12.77 | 19.46 | 22.34 |
| Rg5 | 47.69 | 40.49 | 39.12 |
| PPD | 1.26 | 1.17 | 1.17 |
| Sum | 115.77 | 107.77 | 106.57 |

FIG. 15

| Rare ginsenosides | Contents, mg/g (dry cell weight) | |
|---|---|---|
| | A. stirring | B. non-stirring |
| Rg3 | 44.7 | 43.9 |
| Rh2 | 21.2 | 17.5 |
| Rg5 | 43.1 | 36.4 |
| PPD | 1.1 | 0.5 |
| Sum | 110.1 | 98.3 |

FIG. 16

| Common ginsenosides | Contents, mg/g (dry weight) | | | | |
|---|---|---|---|---|---|
| | A. Wild ginseng CMCs | B. Ginseng | C. Red ginseng | D. Wood-cultivated ginseng | E. Cultured adventitious root of wild ginseng |
| Rg1+Re | 0 | 16.85 | 5.83 | 14.30 | 4.18 |
| Rb1 | 3.01 | 9.55 | 4.21 | 7.73 | 0.87 |
| Rc | 0.98 | 7.91 | 2.76 | 5.84 | 0.30 |
| Rb2 | 2.01 | 2.62 | 1.91 | 1.98 | 0.20 |
| Rd | 0.76 | 1.22 | 0.60 | 0.65 | 0 |
| Gypenoside XVII | 4.07 | 0.06 | 0 | 0.06 | 0.20 |
| F2 | 0.67 | 0.14 | 0 | 0.16 | 0.19 |
| Sum | 11.5 | 38.35 | 15.31 | 30.72 | 5.94 |

FIG. 17

| Rare ginsenosides | Contents, mg/g (dry weight) | | | | |
|---|---|---|---|---|---|
| | A. Wild ginseng CMCs | B. Ginseng | C. Red ginseng | D. Wood-cultivated ginseng | E. Cultured adventitious root of wild ginseng |
| Rg3 | 42.11 | 34.66 | 15.25 | 19.97 | 3.15 |
| Rk1 | 11.84 | 7.00 | 6.59 | 5.69 | 0.99 |
| Rg5 | 24.19 | 13.19 | 15.01 | 12.29 | 1.63 |
| Rh2 | 33.57 | 1.17 | 0.96 | 2.53 | 1.99 |
| Sum | 111.7 | 56.0 | 37.8 | 40.5 | 7.8 |

FIG. 18

Content of converted rare ginsenosides in wild ginseng CMC extract

| Ginsenosides | Contents, mg/L | | | |
|---|---|---|---|---|
| | Before heat treatment | 140°C | 150°C | 160°C |
| Rg1+Re | 101.36 | 0.00 | 0.00 | 0.00 |
| Rb1 | 533.42 | 67.15 | 0.00 | 0.00 |
| Rc | 149.43 | 17.33 | 0.00 | 0.00 |
| Rb2 | 129.09 | 12.36 | 0.00 | 0.00 |
| Rd | 142.42 | 21.91 | 0.00 | 0.00 |
| Gypenoside XVII | 217.52 | 0.00 | 0.00 | 0.00 |
| F2 | 50.29 | 24.88 | 17.49 | 29.15 |
| Sum | 1222.2 | 143.6 | 17.49 | 29.15 |
| Rg3 | 24.10 | 261.03 | 133.92 | 120.77 |
| Rg5 | 8.58 | 256.59 | 134.78 | 220.08 |
| Rh2 | 2.90 | 70.61 | 29.38 | 32.02 |
| PPD | 1.90 | 0.00 | 0.00 | 0.00 |
| Sum | 37.48 | 588.22 | 298.08 | 372.87 |

METHOD FOR PREPARING EXTRACT OF GENUS *PANAX* INCLUDING WILD GINSENG OR GINSENG, OR CAMBIAL MERISTEMATIC CELLS DERIVED FROM GENUS *PANAX* OR EXTRACT THEREOF CONTAINING RARE GINSENOSIDES IN HIGH QUANTITY

CROSS-REFERENCE TO RELATED APPLICATIONS

This application is a U.S. national phase under the provisions of 35 U.S.C. § 371 of International Patent Application No. PCT/KR15/08800 filed Aug. 24, 2015, which in turn claims priority of Korean Patent Application No. 10-2014-0109735 filed Aug. 22, 2014. The disclosures of such international patent application and Korean priority patent application are hereby incorporated herein by reference in their respective entireties, for all purposes.

TECHNICAL FIELD

The present invention relates to a method for increasing the content of rare ginsenosides in preparing an extract of genus *Panax* including wild ginseng or ginseng, cambial meristematic cells derived from genus *Panax* or an extract thereof, a ginseng extract prepared by the method, cambial meristematic cells (CMCs) derived from genus *Panax* or an extract thereof prepared by the method, and to a composition for preventing or treating diabetes, improving blood circulation or improving liver function, comprising the ginseng extract or the cambial meristematic cells (CMCs) derived from genus *Panax* or an extract thereof prepared by the method as an active ingredient.

BACKGROUND ART

Ginseng is a plant belonging to the genus *Panax*, and the root thereof is used for medicinal purposes.

Ginsenosides that are active ingredients present in ginseng are attributable to the medicinal effects of ginseng. Ginsenosides can be classified into three types, i.e., protopanaxadiol-type ginsenosides, protopanaxatriol-type ginsenosides, and oleanane-type ginsenosides according to the structure of ginsenoside aglycone. Ginsenoside derivatives are compounds wherein sugars such as glucose, rhamnose, xylose or arabinose are ester-bonded to the alcoholic OH groups of R1, R2 and R3 of protopanaxadiol or protopanaxatriol that is a triterpene aglycone. The major ginsenosides of ginseng, which are currently known, include about 13 common ginsenosides and about 11 rare ginsenosides known to be converted therefrom.

Ginseng may be used in various forms, including fresh ginseng, white ginseng prepared by drying fresh ginseng, and red ginseng prepared by steaming fresh ginseng.

As is known in the art, fresh ginseng mainly is composed of glycosides ginsenosides, such as Rg1, Re, Rb1, Rb2, Rc, Rd and the like, and processed ginseng may contain increased amounts of rare ginsenosides, such as Rg3, Rh1, Rh2 and Compound K, which are rarely present in fresh ginseng.

Recently many studies have been actively conducted to further increase the content of ginseng saponins present only in processed ginseng products.

Red ginseng, a representative processed ginseng product, may be prepared by steaming fresh, and during the preparation, glycosides bonded to the C-20 position of ginsenoside aglycone, which is chemically unstable, may be hydrolyzed. The amount of ginsenosides such as Rh1, Rh2, Rg2, Rg3 and the like in red ginseng processed by this procedure is larger than that of ginsenosides in fresh ginseng or white ginseng. However, ginsenoside Rh2, a type of rare ginsenoside, is known to be present in a very small amount even in red ginseng.

Since it was reported that the effects of pharmacologically active ingredients of such processed ginseng products on cancer prevention, cancer suppression, blood pressure lowering, protection of brain neurons, anti-thrombosis, antioxidant activities, etc., are better than those of ginseng containing the common ginsenosides, various methods have been attempted to obtain rare ginsenosides which are might be present in processed ginseng. The most well-known methods include methods of increasing the contents of specific ginsenosides either by using microorganisms or by hydrolyzing ginseng saponins with acid and enzyme.

Under this background, the present inventors have found that the contents of desired specific ginsenosides in cambial meristematic cells derived from genus *Panax* can be increased by a method comprising culturing cambial meristematic cells derived from genus *Panax* and heat-treating the cultured cambial meristematic cells derived from genus *Panax*, thereby completing the present invention.

The information disclosed in the Background Art section is only for the enhancement of understanding of the background of the present invention, and therefore may not contain information that forms a prior art that would already be known to a person of ordinary skill in the art.

DISCLOSURE OF INVENTION

Technical Problem

It is an object of the present invention to provide a method for increasing specific ginsenosides, for example, rare ginsenosides rarely present in an untreated genus *Panax* extract or cambial meristematic cells derived from genus *Panax* or an extract thereof or for converting common ginsenosides, present in untreated genus *Panax* extract or cambial meristematic cells derived from genus *Panax* or an extract thereof into rare ginsenosides, in preparing an effective genus *Panax* extract, cambial meristematic cells derived from genus *Panax*, or an extract thereof.

Technical Solution

To achieve the above objects, the present invention provides a method for increasing contents of ginsenoside Rh2 and one or more ginsenosides selected from the group consisting of Rg3, Rk1, Rg5, Rk2, Rh3 and protopanaxadiol (hereinafter referred to as PPD) in preparing cambial meristematic cells (hereinafter, referred to as CMCs) of genus *Panax* or an extract thereof comprising: heat-treating a cultured cambial meristematic cells (CMCs) of genus *Panax* or an extract thereof at a temperature between 85° C. and 160° C.

The present invention also provides a method for increasing contents of ginsenoside Rh2 and one or more ginsenosides selected from the group consisting of Rg3, Rk1, Rg5, Rk2, Rh3 and PPD in preparing—ginseng extract comprising: heat-treating ginseng extract at a temperature between 85° C. and 160° C.

The present invention also provides cambial meristematic cells (CMCs) derived from genus *Panax* or an extract thereof prepared by the method, wherein the contents of ginsenosides Rh2 and one or more ginsenosides selected from the group consisting of Rg3, Rk1, Rg5, Rk2, Rh3 and PPD are increased than those before heat treatment.

The present invention also provides a composition for preventing or treating diabetes comprising the cambial meristematic cells (CMCs) derived from genus *Panax* or the extract thereof, or the ginseng extract as an active ingredient. The present invention also provides a method for preventing or treating diabetes, comprising administering to a subject the above-described cambial meristematic cells derived from genus *Panax* or an extract thereof, or a ginseng extract, or a composition containing the same.

The present invention also provides a composition for improving blood circulation comprising cambial meristematic cells (CMCs) derived from genus *Panax* or the extract thereof, or the ginseng extract as an active ingredient. The present invention also provides a method for improving blood circulation, comprising administering to a subject the above-described cambial meristematic cells derived from genus *Panax* or an extract thereof, or a ginseng extract, or a composition containing the same.

The present invention also provides a composition for improving liver functions comprising the cambial meristematic cells (CMCs) derived from genus *Panax* or the extract thereof, or the ginseng extract as an active ingredient. The present invention also provides a method for improving liver functions, comprising administering to a subject the above-described cambial meristematic cells derived from genus *Panax* or an extract thereof, or a ginseng extract, or a composition containing the same.

BRIEF DESCRIPTION OF THE DRAWINGS

FIG. 10 is a table showing content of converted rare ginsenosides in ginseng extracts.

FIG. 11 is a table showing content of ginsenosides in dried wild ginseng CMCs at various CMC/distilled water ratios.

FIG. 12 is a table showing content of ginsenosides in dried wild ginseng CMCs at various temperatures.

FIG. 13 is a table showing content of ginsenosides in dried wild ginseng CMCs at various times during heat-treatment.

FIG. 14 is a table showing content of ginsenosides at various time periods of static culture.

FIG. 15 is a table showing content of ginsenosides at according to presence and absence of stirring.

FIG. 16 is a table showing content of common ginsenosides in wild ginseng CMCs, ginseng, red ginseng, wood-cultivated ginseng, and cultured adventitious root of wild ginseng.

FIG. 17 is a table showing content of rare ginsenosides in wild ginseng CMCs, ginseng, red ginseng, wood-cultivated ginseng, and cultured adventitious root of wild ginseng.

FIG. 18 is a table showing content of converted rare gensenosides in wild ginseng CMC extract before heat treatment and at various temperatures.

BEST MODE FOR CARRYING OUT THE INVENTION

Figure 1:
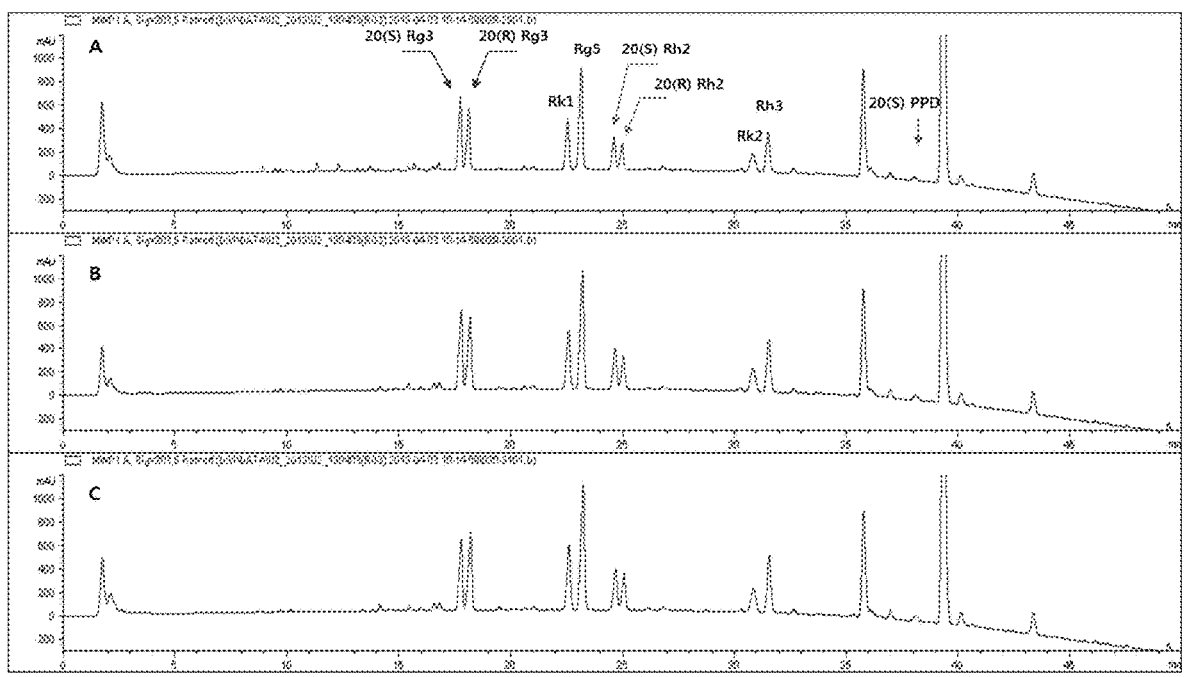
FIG. 1 shows the results of analyzing rare ginsenosides detected by HPLC in the case in which a static culture was performed before heat treatment. A: extraction at 85° C. for 24 hrs; B: extraction at 85° C. for 48 hrs; C: extraction at 85° C. for 72 hrs.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In one aspect, the present invention is directed to a method for increasing contents of ginsenoside Rh2 and one or more ginsenosides selected from the group consisting of Rg3, Rk1, Rg5, Rk2, Rh3 and PPD in preparing cambial meristematic cells (CMCs) of genus *Panax* or an extract thereof comprising: heat-treating a cultured cambial meristematic cells (CMCs) of genus *Panax* or an extract thereof at a temperature between 85° C. and 160° C.

The present invention is also directed to a method for increasing contents of ginsenoside Rh2 and one or more ginsenosides selected from the group consisting of Rg3, Rk1, Rg5, Rk2, Rh3 and PPD in preparing ginseng extract comprising: heat-treating ginseng extract at a temperature between 85° C. and 160° C.

According to the present invention, it is possible to significantly increase the content of rare ginsenosides, particularly Rh2, by a process of heat-treating cultured cambial meristematic cells of genus *Panax* or an extract thereof, but not by a conventional process of either steaming or treating acid, enzyme or microorganism.

As used herein, the term "cambial meristematic cells derived from genus *Panax*" refers to innately undifferentiated cells isolated from the cambial tissue of genus *Panax*, which are characterized in that they are homogeneous cells, have not undergone dedifferentiation into callus, and have meristematic continuity. The present inventors first isolated genus *Panax*-derived cambial meristematic cells which are innately differentiated homogeneous cells, unlike dedifferentiated calluses, from the plant cambium. A method for isolating cambial meristematic cells of genus *Panax* is described in detail in Korean Patent No. 1064518 which may be incorporated herein by reference.

Cambial meristematic cells that are used in the present invention may be, for example, the cambial meristematic cells of white ginseng, wild ginseng or wood-cultivated ginseng, although the types of ginseng that the cambial meristematic cells are derived are not specifically limited, as long as the cells are cambial meristematic cells of genus *Panax* which are innately undifferentiated homogeneous cells, have not undergone dedifferentiation into callus, and have meristematic continuity. The origin of genus *Panax* that may be used in the present invention is not specifically limited. For example, genus *Panax* that is used in the present invention may be ginseng of Korea, USA, Japan, Himalaya, Vietnam or China. Examples of cambial meristematic cells of genus *Panax* that may be used in the present invention include, but are not limited to, whole meristematic cells or their powders, concentrates or extracts. In one embodiment of the present invention, powders or extracts (common ginsenoside extracts) may mainly be used to convert ginsenosides thereof into rare ginsenosides, but any form that is generally commercial in the art may also be used in the practice of the present invention.

Extracts of meristematic cell or ginseng extracts may be prepared by any method which is generally used in the art. For example, the extract may be prepared by mixing 1 part by weight of meristematic cells or dried ginseng with 10-500 parts by weight of distilled water, followed by extraction at a temperature between 50° C. and 100° C.

In this context, the present invention have found that, in case that red ginseng, wood-cultivated ginseng or cultured adventitious root of wild ginseng is used, it cannot be expected that the content of rare ginsenosides such as Rh2 be increased to the desired extent, even when the method of the present invention is applied, but the content of rare ginsenosides such as Rh2 in cambial meristematic cells of genus *Panax* can be significantly increased by a simple process of heat-treating cultured cambial meristematic cells of genus *Panax*.

The ginsenosides such as Rg3, Rk1, Rg5, Rh2, Rk2, Rh3 or PPD are rare ginsenosides that are contained in very small amounts in unprocessed ginseng not treated according to the present invention or that are almost not present or are not present in the unprocessed ginseng. However, according to the method of the present invention, ginsenosides, for example, Rg1, Re, Rb1, Rb2, Rc, Rd, Gypenoside XVII or F2 (hereinafter referred to as common ginsenosides), which are mainly contained in unprocessed ginseng extracts, cambial meristematic cells of genus *Panax* or extracts thereof, are converted into rare ginsenosides by a heat treatment process. Thus, the contents of rare ginsenoside Rh2 and one or more rare ginsenosides selected from the group consisting of Rg3, Rk1, Rg5, Rk2, Rh3 and PPD are increased compared to those in unprocessed (non-heat treated) ginseng extracts, cambial meristematic cells of genus *Panax* or extracts thereof.

In some cases, according to the present invention, the contents of Rh2, Rg3, Rg5 and PPD or all of Rh2, Rg3, Rk1, Rg5, Rk2, Rh3 and PPD, termed as "rare ginsenosides", in cambial meristematic cells of genus *Panax* or an extract thereof, can be increased.

In addition, the contents of Rh2, Rg3, Rg5 and PPD in the ginseng extract may be increased compared to those in non-specifically treated unprocessed (non-heat treated) ginseng extracts.

An increase in the content of rare ginsenosides may refer to the conversion of common ginsenosides into rare ginsenosides by the method of the present invention. Specifically, it may mean that Rh2 and one or more ginsenosides selected from the group consisting of Rg3, Rk1, Rg5, Rk2, Rh3 and PPD are comprised in a ginseng extract, cambial meristematic cells of genus *Panax* or an extract thereof, prepared according to the present invention, in an amount of 80-100 wt % or 90-98 wt % based on the total weight of ginsenosides. If rare ginsenosides such as Rh2 and one or more ginsenosides selected from the group consisting of Rg3, Rk1, Rg5, Rk2, Rh3 and PPD are comprised in an amount of 80-100 wt %, the content of common ginsenosides, for example, Rg1, Re, Rb1, Rb2, Rc, Rd, Gypenoside XVII or F2, may be 20-0 wt %.

If the rare ginsenosides are comprised in an amount of 100 wt % based on the total weight of ginsenosides, it may refer that common ginsenosides contained in a ginseng extract, cambial meristematic cells of genus *Panax* or an extract thereof before treatment were completely converted into rare ginsenosides. Herein, the rare ginsenoside are Rh2 and one or more rare ginsenosides selected from the group consisting of Rg3, Rk1, Rg5, Rk2, Rh3 and PPD.

Herein, Rh2 may be comprised in an amount of 10-35 wt % or 11-33 wt % based on the total weight of Rg3, Rk1, Rg5, Rh2, Rk2, Rh3 and PPD. It has been found that the content of Rh2 in ginseng, wood-cultivated ginseng or cultured adventitious root of wild ginseng is only 3-8% of the content of the rare ginsenoside in a ginseng extract, cambial meristematic cells of genus *Panax* or an extract thereof, prepared according to the present invention, even when the method of the present invention is applied.

The cambial meristematic cells of genus *Panax* may be isolated according to the method disclosed in Korean Patent No. 1064518 of the applicant. The isolated meristematic cells may be cultured by a step of culture for proliferation (proliferation culture) or culture for production (production culture).

A medium that is used for the proliferation culture may be 3% sucrose-containing MS medium (Murashige and Skoog's, 1962). Cambial meristematic cells of genus *Panax* may be seeded in the medium, and then cultured for about 13 days under an air flow rate condition suitable for culture.

A medium that is used for the production culture may be 3% brown sugar-containing modified MS medium. The cambial meristematic cells of genus *Panax* after the proliferation culture may be seeded in the medium, and then treated with an elicitor and cultured for about 11 days under an air flow rate condition suitable for culture.

Examples of elicitors include any substance selected from the group consisting of methyl jasmonate, an extract of fungi, an extract of bacteria, an extract of yeast, chitosan, glucomannan, glucan, phenylalanine, benzoic acid, salicylic acid, arachidonic acid, STS, mevalonate, N-benzoylglycine, ABA, SNP, IPP, BHT, CCC, ethephon, hippuric acid, ammonium ceric nitrate, $AgNO_3$, vanadyl sulfate, p-aminobenzoic acid, brassinosteroids, sodium alginate and sodium acetate. Preferably, methyl jasmonate may be used as elicitor. In this case, methyl jasmonate used as elicitor may be used in an amount of 50-200 μM.

In the cambial meristematic cells of genus *Panax* cultured by the proliferation culture and production culture processes, common ginsenosides, for example, Rg1, Re, Rb1, Rb2, Rc, Rd, Gypenoside XVII or F2, might be present, and rare ginsenosides, for example, Rg3, Rk1, Rg5, Rh2, Rk2, Rh3 or PPD, might not be detected.

The method of the present invention comprises a step of heat-treating the cultured cambial meristematic cells of genus *Panax* or an extract thereof at a temperature between 85° C. and 160° C. Through this step, it is possible to prepare cambial meristematic cells of genus *Panax* or an extract thereof, which contains increased amounts of rare ginsenosides as a result of the conversion of common ginsenosides into rare ginsenosides.

In one embodiment, the method according to the present invention may further comprise, before the heat-treating step, a step of dispersing the cultured cambial meristematic cells of genus *Panax* in distilled water.

In some cases, before dispersion in distilled water, freeze-drying may further be performed. Through freeze-drying, the cells can be conveniently controlled and stored, and a portion of water in the cells and microorganisms or the like, which are present in the water, can be removed, the proliferation of microorganisms by water in the cells can be inhibited.

Distilled water that is used for dispersion of the cambial meristematic cells of genus *Panax* may be used in an amount of 1-200 parts by weight or 30-200 parts by weight per part by weight of the dried cambial meristematic cells of genus *Panax*. When the meristematic cells are used without drying, distilled water may be used in an amount of 2-15 parts by weight or 2.5-10 parts by weight per part by weight of the non-dried meristematic cells.

As the ratio of the amount of distilled water to the amount of cambial meristematic cells of genus *Panax* increases within the above-described range, the content of rare ginsenosides can increase while the content of common ginsenosides decreases.

The method of the present invention may further comprise, after the dispersing step, a step of subjecting the cambial meristematic cells of genus *Panax* dispersed in distilled water to a static culture without shaking.

The static culture may be performed by subjecting the cambial meristematic cells of genus *Panax*, mixed with distilled water, to be in a static status at a temperature of, for example, 1 to 35° C. or 10 to 24° C. for 1-15 days or 2-10 days.

It has been found that the cambial meristematic cells of genus *Panax* prepared by the method comprising this step contain little or no common ginsenosides and contain significantly increased amounts of rare ginsenosides. Particularly, it has been found that, as the static time increases within the above-described range, the content of Rh2 among rare ginsenosides greatly increases.

In another embodiment, the method according to the present invention may further comprise, before the heat-treating step, a step of hot-air-drying the cultured cambial meristematic cells of genus *Panax*. It has been found that the cambial meristematic cells of genus *Panax* prepared by the method comprising this step contain little or no common ginsenosides and contain significantly increased amounts of rare ginsenosides. Particularly, it has been found that the content of Rh2 among rare ginsenosides greatly increases.

The hot-air drying may be performed in a hot-air dryer at a temperature of, for example, 45 to 75° C. or 50 to 70° C. In this case, the hot-air drying may be continued for, for example, 24-72 hours or 30-60 hours. It has been found that the cambial meristematic cells of genus *Panax* prepared by performing hot-air drying within the above-described range contain significantly increased amounts of rare ginsenosides. Particularly, it has been found that the content of Rh2 among rare ginsenosides greatly increases.

The method according to the present invention comprises, after the static culture or hot-air drying, heat-treating the cambial meristematic cells of genus *Panax*. The heat treatment may refer hot-water extraction performed using distilled water at a temperature of 85 to 160° C.

The cambial meristematic cells of genus *Panax* after static culture may be immediately heat-treated at a temperature of 85 to 160° C., because these cells are in a state dispersed in distilled water before static culture. Furthermore, the cambial meristematic cells of genus *Panax* after hot-air drying may further be dispersed in distilled water and heat-treated. Herein, distilled water may be used in an amount of 1-200 parts by weight per part by weight of the dried cambial meristematic cells of genus *Panax* or 30-200 parts by weight per part by weight of the cambial meristematic cells of genus *Panax*.

The heat treatment may be performed by heating the cambial meristematic cells at a temperature of 85-160° C. or 85-115° C. or 95-115° C. According to the present invention, the temperature range suitable for the conversion of common ginsenosides into rare ginsenosides has been determined, and it has been found that the content of rare ginsenosides increases within the above-described temperature range. As the heat-treatment temperature increases within the above-described range, the content of rare ginsenosides might be increased while the content of common ginsenosides decreases, or common ginsenosides might be completely converted into rare ginsenosides.

The heat treatment may be performed for, for example, 10 minutes to 72 hours, or 24 hours to 72 hours, or 48 hours to 72 hours. In the present invention, the heat-treatment time range suitable for the conversion of common ginsenosides into rare ginsenosides has been determined. Specifically, rare ginsenosides were detected in the cambial meristematic cells of genus *Panax* heat-treated within the above-described time range. As the heat treatment time increases within the above-described time range, the content of rare ginsenosides might be increased while the content of common ginsenosides decreases, or common ginsenosides might be completely converted into rare ginsenosides.

The heat treatment may be performed under atmospheric pressure, but the pressure can also increase as the temperature increases. When the heat within the above-described temperature range is applied, the heat-treatment may be, for example, performed under a normal pressure (ranging from 0.57 to 6.1 atm).

The method of the present invention may further comprise a stirring process during the heat treatment. Herein, the stirring may be performed, for example, at 10-200 rpm or 30-180 rpm. When the stirring is performed under this condition, the content of rare ginsenosides can further be increased compared to when the stirring is not performed. In addition, when the stirring is performed, the content of rare ginsenosides can be increased, or the time required for common ginsenosides to be converted into rare ginsenosides can be reduced.

In another aspect, the present invention is directed to cambial meristematic cells of genus *Panax* or an extract thereof, which is prepared by the above-described method and is characterized in that the contents of rare ginsenoside Rh2 and one or more ginsenosides selected from the group consisting of Rg3, Rk1, Rg5, Rk2, Rh3 and PPD are increased than those before heat treatment. In addition, the present invention is directed to a ginseng extract prepared by the above-described method and having increased contents of ginsenoside Rh2 and one or more ginsenosides selected from the group consisting of Rg3, Rk1, Rg5, Rk2, Rh3 and PPD.

The above-described configurations associated with rare ginsenosides or the contents thereof may likewise be applied to the inventions related to cambial meristematic cells of genus *Panax*, an extract thereof and a ginseng extract.

In still another aspect, the present invention is directed to a composition for preventing or treating diabetes, which contains, as an active ingredient, the above-described meristematic cells or an extract thereof, or a ginseng extract. The present invention is also directed to a method for preventing or treating diabetes, comprising administering to a subject the above-described cambial meristematic cells of genus *Panax* or an extract thereof, or a ginseng extract, or a composition containing the same. It has been found that the cambial meristematic cells of genus *Panax*, an extract thereof or a ginseng extract, according to the present invention, which contains increased amounts of rare ginsenosides, exhibits significant glucose tolerance, indicating that it shows anti-diabetic effects.

In addition, the present invention is directed to a composition for improving blood circulation, which contain, as an active ingredient, the above-described meristematic cells or an extract thereof, or a ginseng extract. Besides, the present invention is directed to a method for improving blood circulation, comprising administering to a subject the above-described cambial meristematic cells of genus *Panax* or an extract thereof, or a ginseng extract, or a composition containing the same. It has been found that the cambial meristematic cells of genus *Panax*, an extract thereof or a ginseng extract, according to the present invention, which contains increased amounts of rare ginsenosides, shows an effective ability to inhibit platelet aggregation, indicating that it has a significant effect on improvement in blood circulation.

The above-described blood circulation can be controlled not only by physical factors, including hematocrit, viscosity, blood-induced shear stress, etc., but also by a change in the blood triglyceride composition, hemocytes (platelets), etc. In normal conditions, homeostasis is well maintained, but when blood circulation regulatory function is disturbed by disease conditions such as diabetes, drugs, smoking, etc., plasmas, platelets, erythrocytes, etc., will excessively aggregate, and abnormal haemostasis will occur, thereby interfering with the flow of blood. In addition, it is known that, when activated platelet aggregation is promoted, blood flow homeostasis will be disrupted, and thus blood flow disturbance will cause the onset of arteriosclerosis, stroke, cardiovascular diseases, ischemic heart diseases and cerebrovascular diseases.

The composition for improving blood circulation according to the present invention can inhibit thrombosis to assist in blood circulation improvement, and thus prevent the aging of cells and each organ and promote the growth and regeneration of cells. Specifically, it can improve blood flow to thereby prevent or treat blood circulation disorders, for example, arteriosclerosis, brain hemorrhage, stroke and/or brain infarction, and/or peripheral blood flow disturbance, cold extremities, hair loss symptoms caused by scalp blood circulation disturbance.

In addition, the present invention is directed to a composition for improving liver functions, which contains, as an active ingredient, the above-described cambial meristematic cells of genus *Panax* or an extract thereof, or a ginseng extract. Further, the present invention is directed to a method for improving liver functions, comprising administering to a subject the above-described cambial meristematic cells of genus *Panax* or an extract thereof, or a ginseng extract, or a composition containing the same.

In the present invention, improving liver functions may include, for example, prevention or treatment of fatty liver diseases. The fatty liver diseases may be alcoholic fatty liver disease, non-alcoholic fatty liver disease, nutritional fatty liver disease, starvation fatty liver disease, obesity-induced fatty liver disease, diabetic fatty liver disease or steatohepatitis. In addition, the improvement of liver functions may include the prevention or treatment of liver diseases, for example, liver cirrhosis, alcoholic cirrhosis, fatty liver, toxic liver disease, and acute or chronic hepatitis.

It has been found that the cambial meristematic cells of genus *Panax*, an extract thereof or a ginseng extract, according to the present invention, which has increased contents of rare ginsenosides, exhibits significant effects on the improvement of hepatitis and the alleviation of nonalcoholic fatty liver.

The composition of the present invention may be provided as a pharmaceutical composition containing cambial meristematic cells of genus *Panax*, an extract thereof, or a ginseng extract alone or in combination with at least one pharmaceutically acceptable carrier, excipient or diluent. In addition, the pharmaceutical composition may be administered in a pharmaceutically effective amount depending on the kind of disease and its severity, the patient's age, weight, health condition and sex, the route of administration and the period of treatment. The determination of the composition of the present invention based on such factors depends on the level of a person of ordinary skill in the art. Generally, the composition may be administered at a daily dose of from 0.0001 mg/kg to 2,000 g/kg.

As used herein, the term "pharmaceutically acceptable" refers to a composition that is physiologically acceptable and does not cause gastric disorder, allergic reactions such as gastrointestinal disorder or vertigo, or similar reactions, when administered to humans. Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, magnesium stearate and mineral oils.

The pharmaceutical composition of the present invention may further comprise fillers, anti-aggregating agents, lubricants, wetting agents, perfumes, emulsifiers and preservatives.

Also, the pharmaceutical composition of the present invention may be formulated using a method well known in the art, such that it can provide the rapid, sustained or delayed release of the active ingredient after administration to mammals. The pharmaceutical composition of the present invention may be formulated in the form of powders, granules, tablets, emulsions, syrups, aerosols, soft or hard gelatin capsules, sterile injection solutions, sterile powders, etc.

The cambial meristematic cells of genus *Panax* according to the present invention can be provided in the form of, for example, functional foods. The term "functional foods" as used herein means foods that indicate a function of exhibiting the disease preventing or treating effects by containing the cambial meristematic cells of genus *Panax* as an active ingredient.

The functional foods may be in the form of, for example, powders, granules, tablets, capsules, or beverages. In addition, the functional food may further contain, as acceptable food additives, various nutrients, vitamins, minerals (electrolytes), flavorants such as synthetic flavorants and natural flavorants, coloring agents and improving agents, pectic acid and salts thereof, alginic acid and salts thereof, organic acids, protective colloid thickeners, pH controllers, stabilizers, preservatives, glycerin, alcohols, or carbonating agents.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Ginseng Extract Containing Rare Ginsenosides Converted from Common Ginsenosides 1. Preparation of Ginseng Extract Containing Rare Ginsenosides Converted from Common Ginsenosides

*Panax ginseng* (*Panax ginseng* C.A. Meyer) root extract powder (Xian LVSEN Biotechnology Co., Ltd.) was added to and dissolved in distilled water at a ratio of 30:1 (0.033% concentration), and then heat-treated at 120° C. and normal pressure for 48 hours. The extract was cooled, and only the formed precipitate was collected. The collected precipitate was freeze-dried.

2. HPLC Analysis

For analysis of rare ginsenosides, an Agilent HPLC 1260 DAD system and a Zorbax Eclipse plus C18 (4.6×100 mm, 3.5 μm) column (Agilent) were used under the following conditions: detection wavelength of a DAD detector: UV 203 nm; column temperature: 30° C.; mobile phase: 0.05% trifluoroacetic acid-containing water and acetonitrile; and flow rate: 1 mL/min. In analysis of common ginsenosides and rare ginsenosides, the ratio of the mobile phase was adjusted. Ginsenoside standards used in analysis were purchased from Chromadex (USA), Sigma-Aldrich (USA), and Ambo Institute (Korea). Because standards for the rare ginsenosides Rk2 and Rh3 did not exist, quantitative analysis of Rk2 and Rh3 was not performed, and only the identification of Rk2 and Rh3 by LC/MS was performed. The solvent used in analysis was acetonitrile (Merck, Germany), Methanol (J.T Baker, USA), or Trifluoroacetic acid (Daejung, Korea). Extraction of ginsenosides from each sample was performed using varying methanol/water ratios, and the extract was filtered through a 0.2-μm filter, and then analyzed. Conversion into rare ginsenosides was analyzed, and the results of the analysis are shown in FIG. 10.

Example 2: Preparation of Wild Ginseng Cambial Meristematic Cell (CMC) Powder Containing Rare Ginsenosides Converted from Common Ginsenosides 1. Culture of Wild Ginseng CMCs From the cambium of *Panax Ginseng* (wild ginseng, Gangwon-do, Korea), wild ginseng CMCs were isolated. Culture of the wild ginseng CMCs was progressively scaled up from a 250 mL flask to a 3 L bioreactor, a 20 L bioreactor and a 250 L bioreactor.

In a general plant cell culture, 2,4-dichlorophenoxyacetic acid or naphthaleneacetic acid is used as a cell growth regulator for inducing cell division. However, wild ginseng CMCs are cultured under established proliferation culture conditions in the absence of the growth regulator. Regarding proliferation culture conditions for keeping the fresh weight of wild ginseng CMCs, MS medium containing 3% sucrose was used (Murashige and Skoog's, 1962), and the pH of the MS medium was adjusted to 5.8, and culture was performed for 13 days.

After completion of the proliferation culture, production culture was performed in modified MS medium containing 3% brown sugar for 11 days after treatment with 100 μM methyl jasmonate. The proliferation culture and the production culture were performed in the same culture room, and the culture room was maintained at a temperature of 21±1° C. under dark conditions.

2. Preparation of CMCs Containing Rare Ginsenosides Converted from Common Ginsenosides After biomass and common ginsenosides (Rb1, Rb2, Rc, and Rd) were obtained through the proliferation culture and the production culture, the cells were subjected to be in a static culture in the culture room for 5 days under air-off conditions. To obtain rare ginsenosides, including Rg3, Rk1, Rg5, Rh2, PPD and the like, the cells were heat-treated in an extractor. After common ginsenosides were converted into rare ginsenosides (Rg3, Rk1, Rg5, Rh2, Rk2, Rh3 and PPD) by the heat-treatment process, the biomass was collected, and then dried (freeze-dried or hot-air-dried).

3. HPLC Analysis

Analysis of rare ginsenosides in the wild ginseng CMCs was performed in the same manner as described in Example 1.

Experimental Example 1: Comparison in Ratio of Conversion into Rare Ginsenoside According to Various Ratios of Water Used in Extraction During Example 2-2 after Example 2-1, mixtures of 1 part by weight of dried wild ginseng CMCs and 20-200 parts by weight of distilled water were heat-treated in an extractor at 85° C. for 24 hours to determine a CMC/distilled water ratio suitable for the conversion of common ginsenosides into rare ginsenosides.

Referring to FIG. 11, it can be seen that, under the conditions of heat treatment temperature of 85° C. and heat treatment time of 24 hours, the contents of most of common ginsenosides in the wild ginseng CMCs decrease as the ratio of distilled water increases.

Experimental Example 2: Comparison in Ratio of Conversion into Rare Ginsenoside According to Heat-Treatment Temperatures During Example 2-2 after Example 2-1, a mixture of 1 part by weight of dried wild ginseng CMCs and 100 parts by weight of distilled water was heat-treated in an extractor at a temperature ranging from 85° C. to 115° C. for 24 hours to determine a temperature suitable for the conversion of common ginsenosides into rare ginsenosides.

Referring to FIG. 12, it can be seen that, under the conditions of CMC/water ratio of 1:100 and heat-treatment condition of 24 hours, the contents of most of common ginsenosides in the wild ginseng CMCs decrease as the heat-treatment temperature increases.

Experimental Example 3: Comparison in Ratio of Conversion into Rare Ginsenoside According to Heat-Treatment Time During Example 2-2 after Example 2-1, a mixture of 1 part by weight of dried wild ginseng CMCs and 100 parts by weight of distilled water was heat-treated in an extractor at a temperature of 85° C. for 24-72 hours to determine a temperature suitable for the conversion of common ginsenosides into rare ginsenosides.

Referring to FIG. 13, it can be seen that, under the conditions of CMC/water ratio of 1:100 and heat-treatment temperature of 85° C., the most of common ginsenosides in the wild ginseng CMCs are almost not present as the heat-treatment temperature increases.

Figure 2:
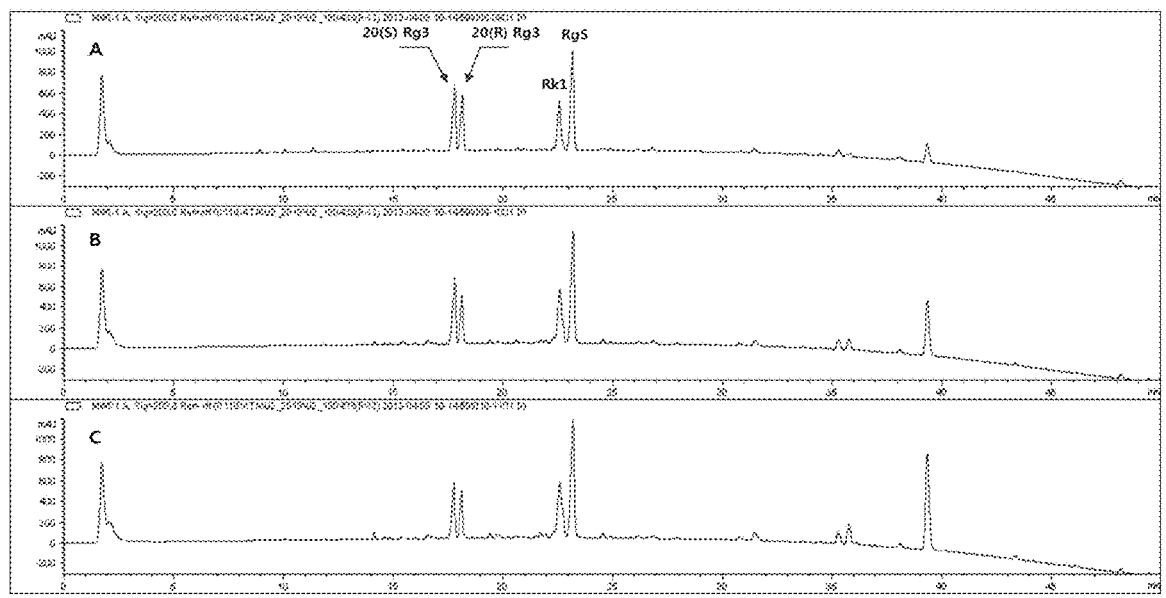
FIG. 2 shows the results of analyzing rare ginsenosides detected by HPLC in the case in which no static culture was performed before heat treatment (A: extraction at 85° C. for 24 hrs; B: extraction at 85° C. for 48 hrs; and C: extraction at 85° C. for 72 hrs).

Experimental Example 4: Comparison in Productivity of Rare Ginsenoside According to Presence and Absence of Static Culture Additional wild ginseng CMCs were prepared in the same manner as described in Example 2-2, except that the static culture before heat treatment was not performed. The results obtained when the static culture before heat treatment was performed for 5 days are shown in FIGS. 1 and 2 in comparison with those obtained when the static culture was not performed. Referring to FIGS. 1 and 2, it can be seen that, when the static culture was performed, the contents of Rh2 and PPD among rare ginsenosides increased (see FIG. 1), unlike when the static culture was not performed (see FIG. 2).

Figure 3:
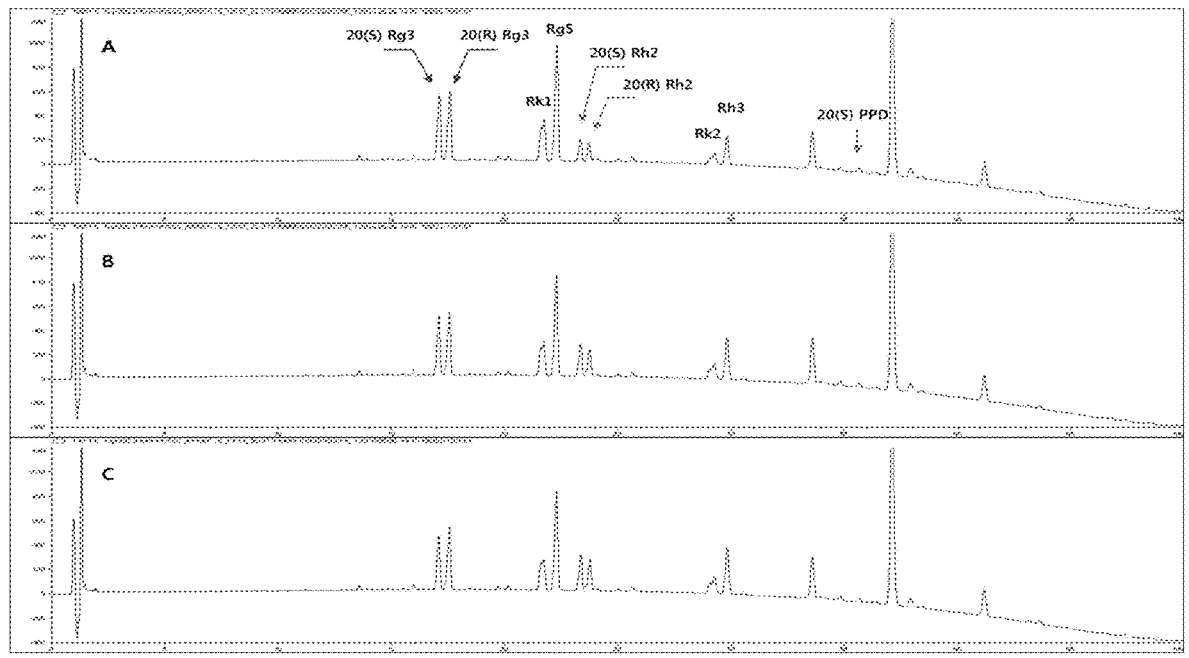
FIG. 3 shows the results of analyzing rare ginsenosides detected by HPLC as a functional of the static time before heat treatment.

Experimental Example 5: Comparison in Productivity of Rare Ginsenosides According to Static Time Wild ginseng CMCs were prepared in the same manner as described in Example 2-2 (heat treatment at 95° C. for 48 hrs), and the contents of rare ginsenosides, obtained for varying static time periods, are shown in FIG. 3 and FIG. 14. Referring to FIG. 3 and FIG. 14, it can be seen that the content of Rh2 among rare ginsenosides increased as the static time period increases.

Figure 4:
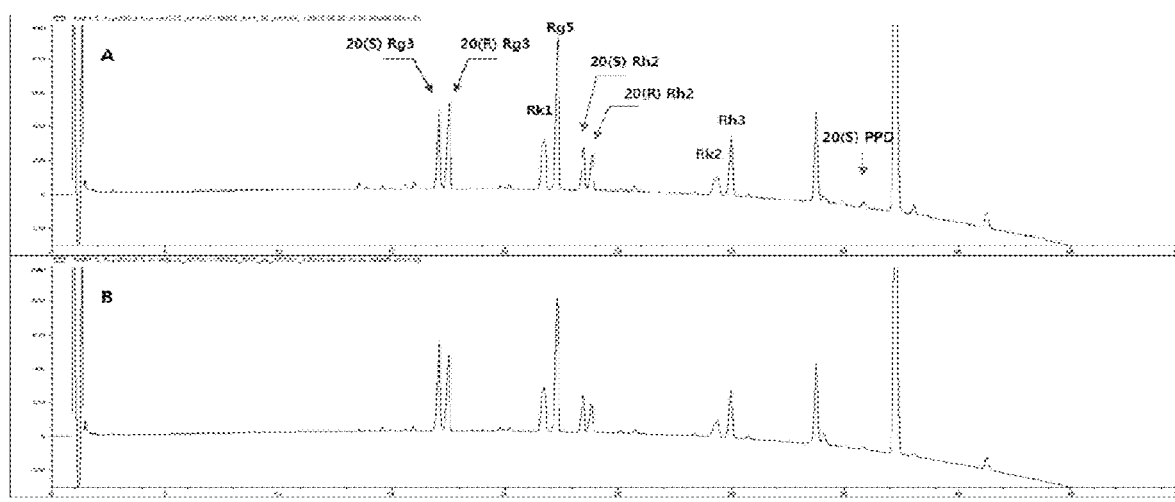
FIG. 4 shows the results of analyzing rare ginsenosides detected by HPLC in the case in which stirring was performed or not performed.

Experimental Example 6: Comparison in Productivity of Rare Ginsenosides According to Presence and Absence of Stirring In Example 2, a mixture of 1 part by weight (a fresh weight basis) of wild ginseng CMCs and 2.5-10 parts by weight of distilled water (50-200 parts by weight of distilled water per part by dry weight of CMCs) was stirred at 30-180 rpm while it was heat-treated at 95° C. for 48 hrs, and whether or not the contents of rare ginsenosides were changed by the stirring process was examined. Referring to FIG. 4 and FIG. 15, it can be seen that, when stirring is performed, the contents of rare ginsenosides such as Rg3, Rh2, Rg5 and PPD are higher than when stirring is not performed.

Example 3: Carrying Out of Hot-Air Drying and Heat Treatment

Wild ginseng CMCs were prepared in the same manner as described in Example 2-1. The prepared CMCs were hot-air dried in HK-06H (Korea Technology Eng, Co., Ltd.) under 60° C./48 hr, then powdered (120 mesh), followed by adding 1 part by weight of the powder to 100 parts by weight of distilled water and subjecting to hot-water extraction at 95° C. for 48 hrs. In addition, ginseng, red ginseng, wood-cultivated ginseng and cultured adventitious root of wild ginseng were also heat-treated under the same conditions as described above. The results are shown in FIGS. 5, 6, 16, and 17.

Figure 5:
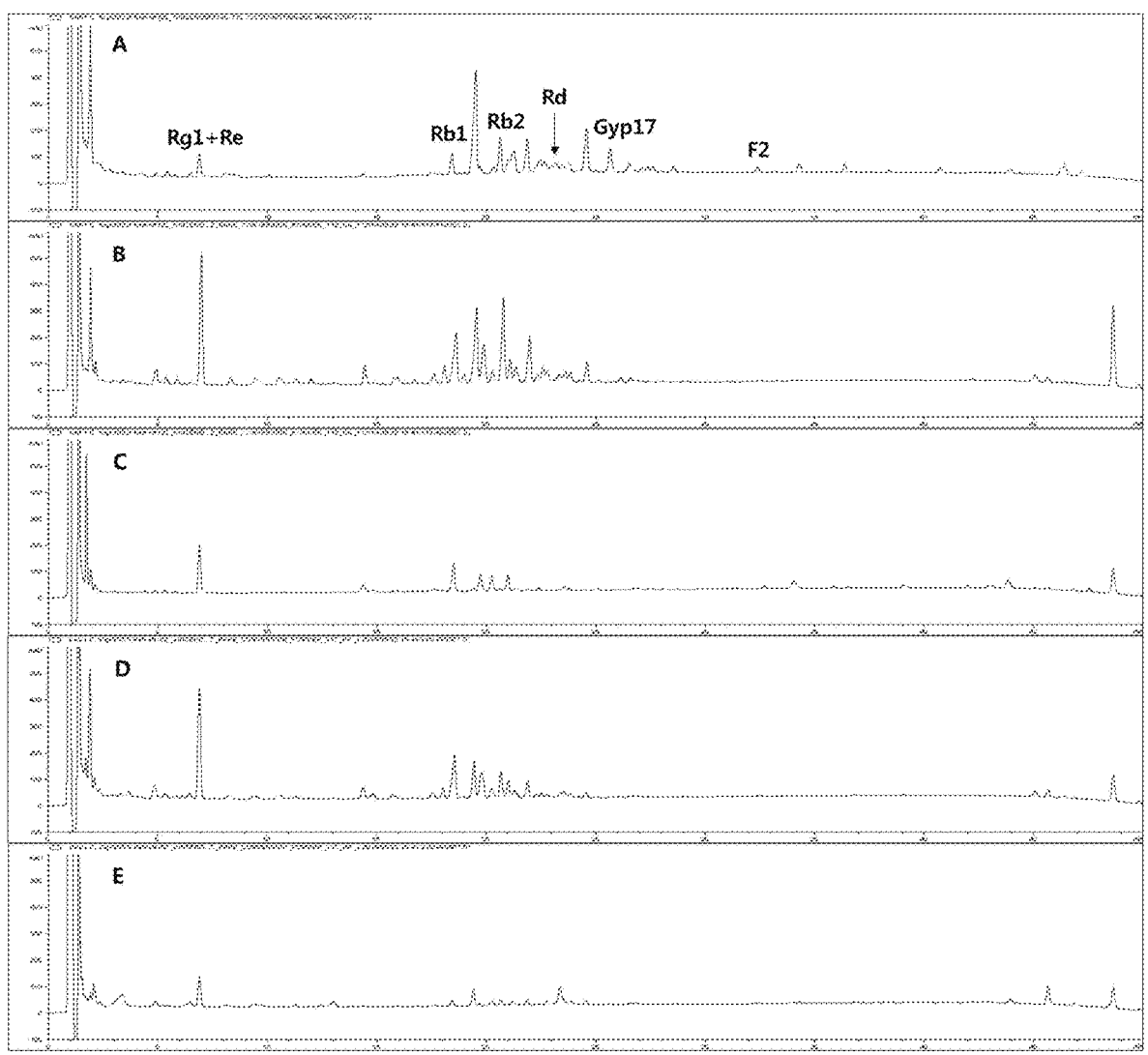
FIG. 5 shows the results of analyzing common ginsenosides of a sample including wild ginseng CMCs, ginseng, red ginseng, wood-cultivated ginseng or cultured adventitious root of wild ginseng before heat treatment (A: wild ginseng CMCs; B: ginseng; C: red ginseng, D: wood-cultivated ginseng, E: cultured adventitious root of wild ginseng).

Referring to FIG. 5 and FIG. 16, it can be seen that the contents of common ginsenosides such as Gypenoside XVII and F2 in the hot-air-dried wild ginseng CMCs are higher than those in other ginseng products and that when heat treatment is performed, the content of Rh2 in the wild ginseng CMCs is significantly higher than that in other ginseng products. Furthermore, ginseng, wood-cultivated ginseng and cultured adventitious root of wild ginseng, except for red ginseng, were purchased in a non-dried (fresh) state and hot-air-dried under the same conditions as described above, but an increase in the contents of common ginsenosides such as Gypenoside XVII and F2 that might influence the production of the rare ginsenoside Rh2 could not be observed, and it could be seen that the content of the rare ginsenoside Rh2 therein was very low, even though heat is treated.

This seems to be because structures such as Gypenoside XVII and F2, which have one glucose molecule attached to the C-3 carbon position, are advantageous for obtaining Rh2. Specifically, in the case of Gypenoside XVII and F2, two glucose molecules and one glucose molecule respectively are attached to the C-20 carbon positions, and one glucose molecule is attached to the C-3 carbon position. It appears that Rh2 is obtained when the glucose molecules attached to the C-20 carbon position are easily detached by heat and only one glucose molecule remains attached to the C-3 carbon position. For this reason, the above-described results are obtained.

Figure 6:
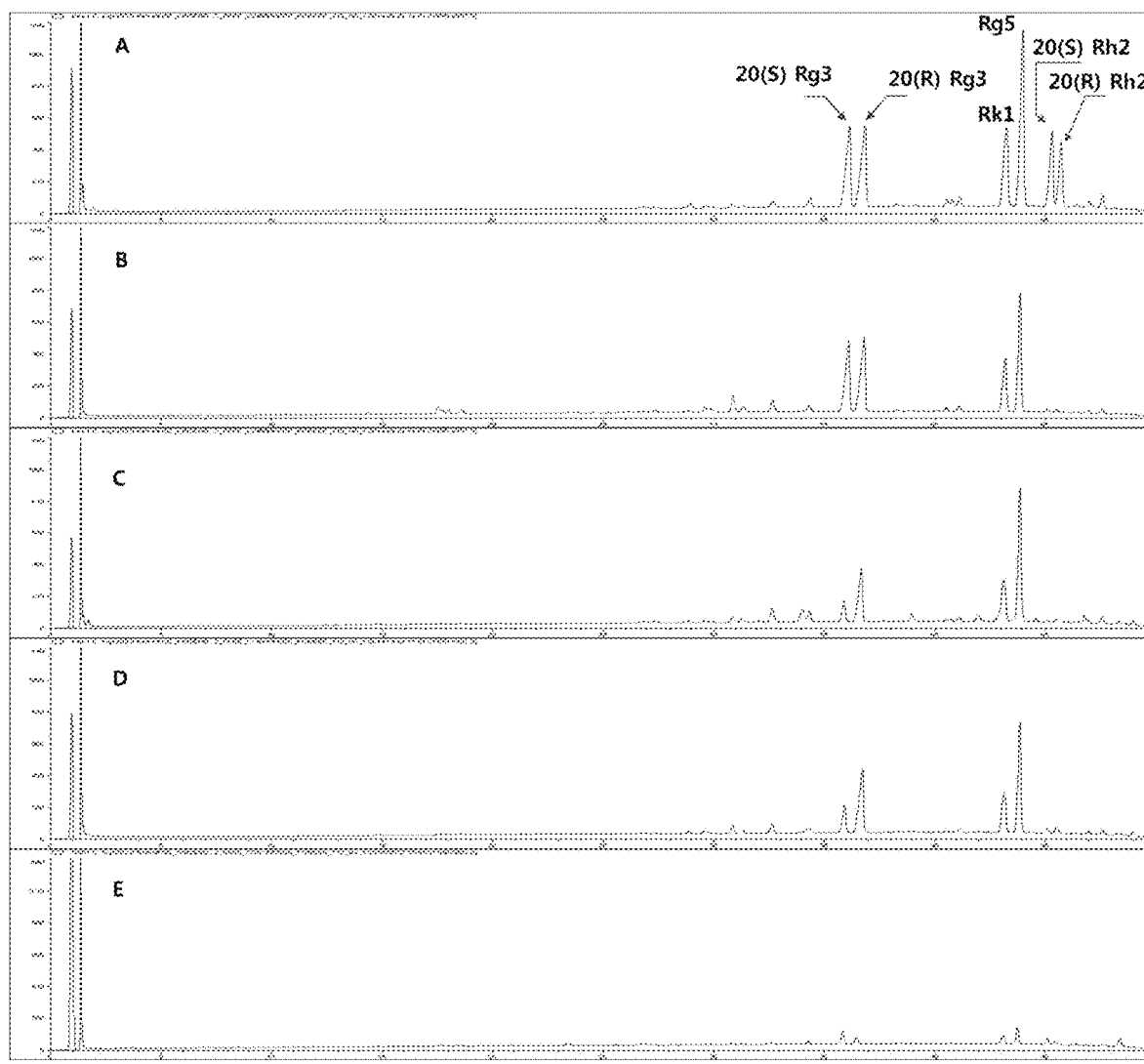
FIG. 6 shows the results of analyzing detected rare ginsenosides of a sample including wild ginseng CMCs, ginseng, red ginseng, wood-cultivated ginseng or cultured adventitious root of wild ginseng after hot-air drying and heat treatment (A: wild ginseng CMCs; B: ginseng; C: red ginseng, D: wood-cultivated ginseng, E: cultured adventitious root of wild ginseng).

Moreover, as shown in FIG. 6 and FIG. 17, the heat-treatment method according to the present invention can convert most of common ginsenosides into rare ginsenosides. Non-dried (fresh) wild ginseng CMCs are heated at the cell level, whereas the heat is conducted in a powdered state for freeze-dried and hot-air-dried wild ginseng CMCs, and thus have high heat transfer efficiency and have superiority in terms of conversion into rare ginsenosides. For example, red ginseng is prepared by steaming fresh ginseng in a state in which the characteristic form of fresh ginseng is maintained. It can be seen that the contents of most rare ginsenosides in red ginseng are low and the contents of common ginsenosides are high. However, when fresh ginseng is powdered and the heat-treatment method according to the present invention is applied, it can be seen that most of common ginsenosides are converted into rare ginsenosides and the content of the rare ginsenoside Rg3 is also high.

As described above, unlike conventional red ginseng, fresh ginseng, wood-cultivated ginseng or cultured adventitious root of wild ginseng, the wild ginseng CMCs obtained by the method of the present invention has significantly increased contents of rare ginsenosides, including Rh2. As heat is treated at the cell level of wild-ginseng CMCs or product of grinding or powdering after drying has a particle size ranging from several hundreds of nm to several tens of μm, thus heat transfer efficiency is high. This leads to easy detachment of sugar molecules attached to the C-20 carbon position of the aglycone PPD.

Various attempts have been made to increase the content of rare ginsenosides. However, when red ginseng, fresh ginseng, wood-cultivated ginseng or cultured adventitious root of wild ginseng is used, it undergoes various treatments (treatment with heat, enzyme, acid, base or the like) at the tissue level. For this reason, it appears that the efficiency of removal of sugar from the C-20 position is very low, and an increase in the content of rare ginsenosides is very low.

Example 4: Wild Ginseng CMC Extract Containing Rare Ginsenosides Converted from Common Ginsenosides 1. Preparation of Wild Ginseng CMC Extract Containing Rare Ginsenosides Converted from Common Ginsenosides A mixture of 1 part by dry weight of dried wild ginseng CMCs and 50-200 parts by weight of distilled water was extracted at 75° C. for 18 hours. The extract was separated from the wild ginseng CMCs and filtered through a 0.2 μm filter, thereby preparing a wild ginseng CMC extract. The prepared wild ginseng CMC extract was heat-treated in an autoclave (MSR-3L-150/250-MD-S6-SYS, Phos-Entech, Co., Ltd.) at 140° C., 150° C. or 160° C. and normal pressure for 60 minutes. The wild ginseng CMC extract was cooled, and the formed precipitate was collected and freeze-dried.

2. HPLC Analysis

Analysis of rare ginsenosides in the wild ginseng CMC extract was performed in the same manner as described in Example 1. Conversion into rare ginsenosides was analyzed, and the results of the analysis are shown in FIG. 18.

Experimental Example 7: Anti-Diabetic Effect of Wild Ginseng CMCs

The anti-diabetic effect of the wild ginseng CMCs prepared in Example 2 was examined by an oral glucose tolerance test OGTT. Wild ginseng CMCs were heat-treated at 95° C. for 48 hours, and an extract obtained by extracting the CMCs with 70% ethanol was administered orally. C57BL/6J mice (8-week-old, male) were fasted overnight. The weights and blood glucose levels of the C57BL/6J mice were measured, and then 2 g/kg of D-glucose was administered orally to the mice. At this time, the mice were fed with drinking water, but were not fed with feed. A change in the blood glucose level was measured at 2-hr intervals for 2 hours.

Figure 7:
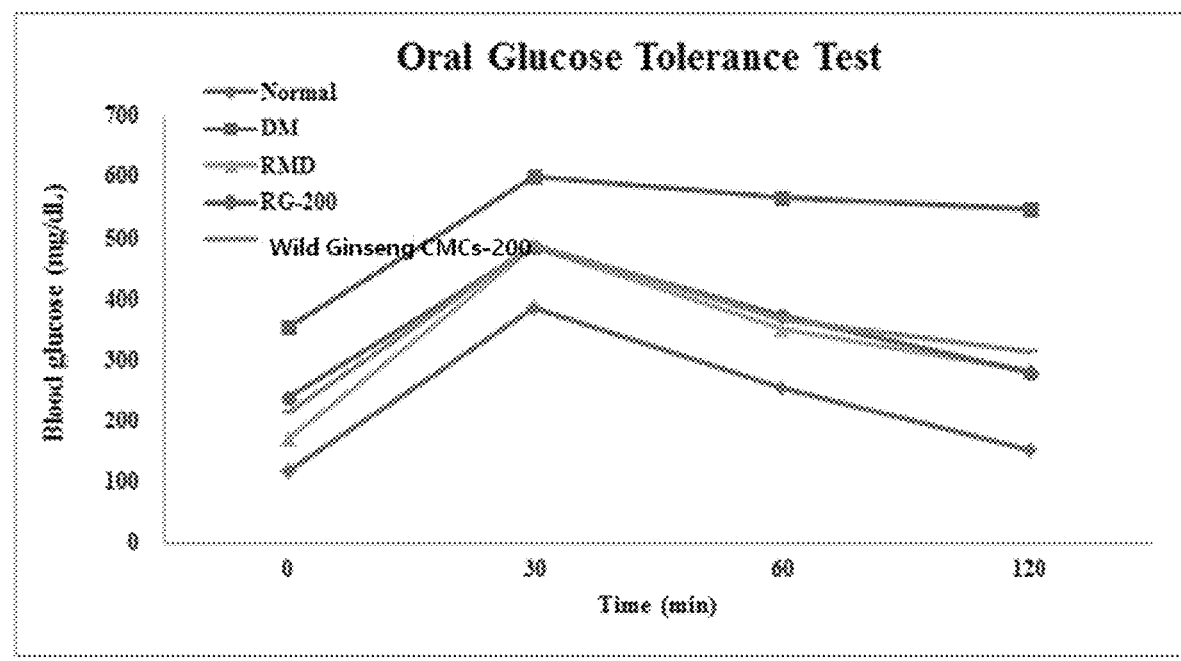
FIG. 7 shows the results of an oral glucose tolerance test (OGTT) performed to confirm the anti-diabetic effect of wild ginseng CMCs prepared according to an example of the present invention.

The results of the measurement are shown in FIG. 7 and Table 1 below. When D-glucose was administered orally, the diabetic group showed little or no glucose tolerance, unlike the normal group. The red ginseng CMC extract was compared with resistant maltodextrin (RMD) and a red ginseng extract (RG-200), which are known as health supplements in the anti-diabetic field. As a result, it was shown that the wild ginseng CMCs (wild ginseng CMCs-200) showed glucose tolerance (anti-diabetic effect) comparable to that shown in the samples known as health supplements.

TABLE 10

| Blood glucose level (mg/dL) | | | | |
|---|---|---|---|---|
| Time | Normal | DM | RMD | RG-200 | Wild ginseng CMCs-200 |
| 0 | 118 | 354 | 169 | 239 | 214 |
| 30 | 386 | 600 | 485 | 486 | 489 |
| 60 | 255 | 567 | 350 | 372 | 368 |
| 120 | 152 | 547 | 282 | 279 | 315 |

DM: untreated diabetic group, RMD: Resistant maltodextrin (2 g/kg)-treated diabetic group, RG-200: Red Ginseng extract (200 mg/kg)-treated diabetic group, Wild Ginseng CMCs-200: Wild Ginseng CMCs extract (200 mg/kg)-treated diabetic group.

Experimental Example 8: Effect of Wild Ginseng CMCs on Improvement in Blood Circulation An anti-platelet assay for the wild ginseng CMCs prepared in Example 2 was performed. Wild ginseng CMCs heat-treated at 95° C. for 48 hrs were extracted with 70% ethanol, and the wild ginseng CMC extract was administered orally.

3.2% Trisodium citrate was prepared and mixed with blood, taken from abdominal aorta, at a ratio of 1:9 (v/v). The mixture was allowed to stand in a roll mixer for 10 minutes, and then centrifuged at 1000 rpm and at room temperature for 10 minutes, and then the supernatant was collected (platelet rich plasma; PRP). Using PPP, the platelet number of PRP was counted, and PRP was diluted at a concentration of 250-400×10$^3$ platelets/mL, and the dilution was allowed to stand in a roll mixer for 5 minutes. In an aggregometer (Chrono-log, USA), PRP or sample-added PRP was pre-heated to 37° C., and then an agonist (ADP, collagen, etc) that induces platelet aggregation was dropped into the PRP. Next, using PPP as a control, a change in turbidity was measured to determine aggregation rate (%) (100: the highest aggregation; 0: the lowest aggregation). Percent inhibition can be expressed as the following equation.

Inhibition (%)=(inhibition (%) of PRP alone−inhibition (%) of PRP/sample mixture/inhibition (%) of PRP alone×100

Figure 8:
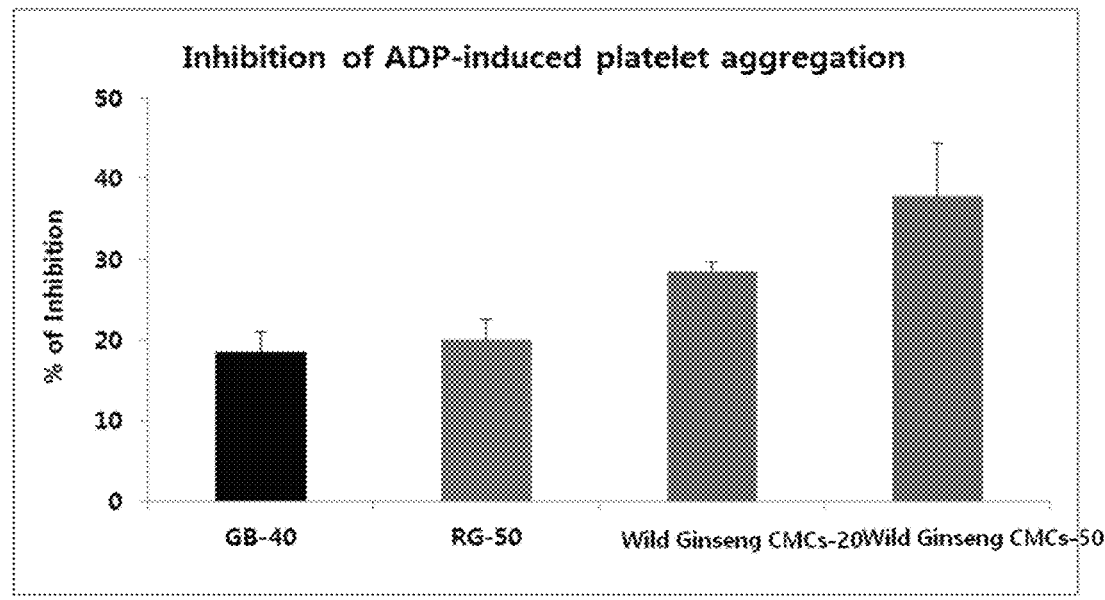
FIG. 8 shows the results of an anti-platelet assay for wild ginseng CMCs prepared according to an example of the present invention.

The results are shown in FIG. 8 and Table 2. As a control, a ginkgo leaf extract (GB-40) and a red ginseng extract (RG-50), known as health supplements in the blood circulation improvement field, were used. The results of comparison with the control indicated that the wild ginseng CMC extracts (wild ginseng CMCs-20, and wild ginseng CMCs-50) had excellent blood circulation effects compared to the samples known as health supplements.

TABLE 11

| Percent inhibition of platelet aggregation | | | |
|---|---|---|---|
| | GB-40 | RG-50 | Wild ginseng CMCs-20 | Wild ginseng CMCs-50 |
| % of inhibition | 18.5 | 20.1 | 28.5 | 37.8 |

GB-40: Gingko leaf extract (40 mg/kg)-treated group, RG-50: Red Ginseng extract (50 mg/kg)-treated group, Wild Ginseng CMCs-20: Wild Ginseng CMCs extract (20 mg/kg)-treated group, Wild Ginseng CMCs-50: Wild Ginseng CMCs extract (50 mg/kg)-treated group.

Experimental Example 9: Effect of Wild Ginseng CMCs on Improvement in Liver Function 1. Liver Function Improvement Effect Against GalN-Induced Hepatitis Freeze-dried wild ginseng CMCs were dissolved in sterile saline and administered orally via a sonde. 7-week-old male Sprague-Dawley rats were fasted for 18 hours, and GalN (700 mg/kg PBS) was administered intraperitoneally to the mice. After 24 hours, blood and liver tissue were extracted from the mice, and serum ALT and AST activities were measured. The test sample was administered orally to the mice once a day at the same appointed time for 14 days before administration of GalN. On the day of administration of GalN, the test sample was administered orally at 2 hours before administration and at 6 hours after administration of GalN.

Figure 9:
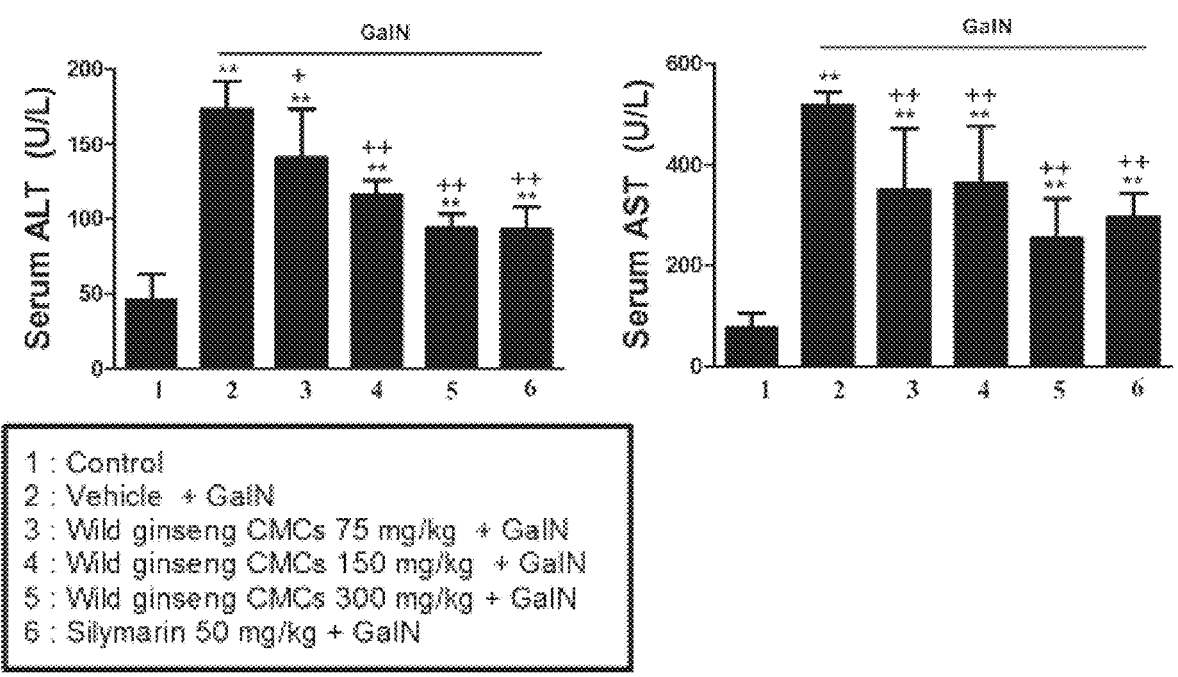
FIG. 9 shows the effect of evaluating the hepatitis-related liver function improvement effect of wild ginseng CMCs prepared according to an example of the present invention (ALT, alanine aminotransferase; AST, aspartate aminotransferase; GalN, D-galactosamine).

Referring to FIG. 9, it was shown that the serum ALT and AST levels in the GalN-induced models treated with 75, 150 and 300 mg/kg of the wild ginseng CMCs for 2 weeks were significantly inhibited compared to the group treated with the positive control silymarin.

2. Effect on Improvement of Nonalcoholic Fatty Liver

Wild ginseng CMCs were suspended in distilled water, and then administered orally via a sonde for 10 weeks. High-fat diet was administered to 57BL/6 mice (22-26 g) for 10 weeks to induce fatty liver. Each animal group was allowed access to solid feed, high-fat diet feed (Research Diets, Inc., New Brunswick, N.J., USA) and water ad libitum.

Referring to Table 3, it can be seen that administration of the wild ginseng CMCs greatly reduced body weight, serum and hepatic triglyceride levels, and serum ALT activity.

TABLE 12

Effects of wild ginseng CMCs on the body weight, triglyceride level and serum ALT activity of high-fat diet-fed mice

| Group | Body weight (g) | Hepatic TG (mg/g liver) | Hepatic TC (mg/g liver) | Serum TG (mg/dl) | Serum TC (mg/dl) | ALT (U/l) |
|---|---|---|---|---|---|---|
| NFD | 31.5 | 14.2 | 17.2 | 83.4 | 141.0 | 36.6 |
| HFD | 44.6 | 20.7 | 26.8 | 111.2 | 173.2 | 45.5 |
| HFD75 | 35.4 | 15.1 | 18.6 | 75.2 | 156.2 | 40.2 |
| HFD 150 | 33.8 | 14.0 | 14.6 | 72.0 | 143.5 | 35.8 |
| HFD 300 | 33.2 | 14.8 | 19.8 | 82.6 | 150.0 | 29.0 |
| HFD sily | 34.9 | 11.7 | 15.4 | 72.8 | 145.2 | 31.8 |

8 to 10 mice per group. ALT, alanine aminotransferase; HFD, high fat diet; NFD, normal fat diet; TC, total cholesterol; TG, triglyceride; HFD 75, HFD + wild ginseng CMCs 75 mg/kg; HFD 150, HFD + wild ginseng CMCs 150 mg/kg; HFD 300, HFD + wild ginseng CMCs 300 mg/kg; HFD sily, HFD + silymarin 100 mg/kg.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, according to the method of the present invention, cambial meristematic cells of genus *Panax*, an extract thereof, or a ginseng extract, which contains an increased amount of one or more rare ginsenosides selected from the group consisting of highly pharmacologically active Rg3, Rk1, Rg5, Rh2, Rk2, Rh3 and PPD, can be efficiently prepared by a simple process.

What is claimed is:

1. A method of preparing cambial meristematic cells (CMCs) of genus *Panax* or an extract thereof, comprising:
    dispersing cambial meristematic cells (CMCs) of genus *Panax* in distilled water in an amount of 30-200 parts by weight per part by weight of the cambial meristematic cells (CMCs) of genus *Panax*;
    subjecting the cambial meristematic cells (CMCs) of genus *Panax* dispersed in distilled water to a static culture without shaking; and
    heat-treating the cambial meristematic cells (CMCs) of genus *Panax* or an extract thereof at a temperature between 85° C. and 160° C., in which contents of ginsenoside Rh2 and one or more ginsenosides selected from the group consisting of Rg3, Rk1, Rg5, Rk2, Rh3 and PPD are increased.

2. The method of claim 1, wherein the contents of ginsenosides Rh2, Rg3, Rk1, Rg5, Rk2, Rh3 and PPD in the cambial meristematic cells (CMCs) of genus *Panax* are increased compared to those of ginsenosides before heat treatment.

3. The method of claim 1, wherein Rh2 and one or more ginsenosides selected from the group consisting of Rg3, Rk1, Rg5, Rk2, Rh3 and PPD are comprised in an amount of 80-100 wt % based on the total weight of ginsenosides.

4. The method of claim 1, wherein Rh2 is comprised in an amount of 10-35 wt % based on the total weight of Rg3, Rk1, Rg5, Rh2, Rk2, Rh3 and PPD.

5. The method of claim 1, wherein the contents of ginsenosides Rh2, Rg3 and Rg5 in the extract of cambial meristematic cell of genus *Panax* are increased compared to those of ginsenosides before heat treatment.

6. The method of claim 1, wherein the static culture is performed at a temperature of 1 to 35° C. for 1-15 days.

7. The method of claim 1, further comprising a freeze-drying step before the static culture.

8. The method of claim 1, further comprising, before the heat-treating step, a step of hot-air-drying the cultured cambial meristematic cells (CMCs) of genus *Panax*.

9. The method of claim 8, wherein the hot-air drying is performed at a temperature of 45 to 75° C. for 24-72 hours.

10. The method of claim 1, wherein the heat-treating is performed for 10 minutes to 72 hours.

11. The method of claim 1, further comprising a step of stirring at 10-200 rpm during the heat treatment.

12. The method of claim 1, wherein the ginseng is white ginseng, wild ginseng or wood-cultivated ginseng.

13. A method for treating diabetes comprising administering the cambial meristematic cells (CMCs) of genus *Panax* or the extract thereof prepared by the method of claim 1 as an active ingredient, wherein contents of ginsenoside Rh2 and one or more ginsenosides selected from the group consisting of Rg3, Rk1, Rg5, Rk2, Rh3 and PPD is in an amount of 80-100 wt % based on total weight of ginsenosides.

14. A method for improving blood circulation comprising administering the cambial meristematic cells (CMCs) of genus *Panax* or the extract thereof prepared by the method of claim 1 as an active ingredient, wherein contents of ginsenoside Rh2 and one or more ginsenosides selected from the group consisting of Rg3, Rk1, Rg5, Rk2, Rh3 and PPD is in an amount of 80-100 wt % based on total weight of ginsenosides.

15. A method for improving liver functions comprising administering the cambial meristematic cells (CMCs) of genus *Panax* or the extract thereof prepared by the method of claim 1 as an active ingredient, wherein contents of ginsenoside Rh2 and one or more ginsenosides selected from the group consisting of Rg3, Rk1, Rg5, Rk2, Rh3 and PPD is in an amount of 80-100 wt % based on total weight of ginsenosides.

* * * * *

UNITED STATES PATENT AND TRADEMARK OFFICE
CERTIFICATE OF CORRECTION

PATENT NO. : 10,646,528 B2
APPLICATION NO. : 15/502423
DATED : May 12, 2020
INVENTOR(S) : Jin et al.

Page 1 of 1

It is certified that error appears in the above-identified patent and that said Letters Patent is hereby corrected as shown below:

In the Specification

Column 15, Line 50: "TABLE 10" should be -- TABLE 1 --.

Column 16, Line 34: "TABLE 11" should be -- TABLE 2 --.

Column 17, Line 13: "TABLE 12" should be -- TABLE 3 --.

Signed and Sealed this
Sixteenth Day of June, 2020

Andrei Iancu
*Director of the United States Patent and Trademark Office*